(12) United States Patent
Turner et al.

(10) Patent No.: US 7,681,453 B2
(45) Date of Patent: Mar. 23, 2010

(54) SYSTEM AND METHOD TO CALIBRATE MULTIPLE SENSORS

(75) Inventors: Wesley David Turner, Rexford, NY (US); Christopher Allen Nafis, Rexford, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 87 days.

(21) Appl. No.: 11/092,390

(22) Filed: Mar. 29, 2005

(65) Prior Publication Data

US 2006/0219014 A1    Oct. 5, 2006

(51) Int. Cl.
*G01N 29/04* (2006.01)
(52) U.S. Cl. .......................................... 73/657; 356/502
(58) Field of Classification Search .................... 73/643, 73/657, 1.86, 1.82; 356/4.02, 502, 243.4, 356/243.5, 243.7
See application file for complete search history.

(56) References Cited

U.S. PATENT DOCUMENTS

| | | | | |
|---|---|---|---|---|
| 5,505,090 | A * | 4/1996 | Webster | 73/657 |
| 5,684,592 | A * | 11/1997 | Mitchell et al. | 356/493 |
| 6,321,601 | B1 * | 11/2001 | Maris | 73/657 |
| 6,542,185 | B1 * | 4/2003 | Bogardus | 348/223.1 |
| 6,633,384 | B1 * | 10/2003 | Drake et al. | 356/432 |
| 6,850,858 | B1 * | 2/2005 | West et al. | 702/104 |

* cited by examiner

*Primary Examiner*—John E Chapman
(74) *Attorney, Agent, or Firm*—Bracewell & Giuliani LLP (57) ABSTRACT

The present invention provides a multi-mode calibration target operable to calibrate multiple optical sensors. One embodiment has multiple planar surfaces, wherein the multiple planar surfaces are able to be distinguished by visual sensors based on their color, hue, shade, tint, or tone. Additionally, these planar surfaces may be raised or recessed from one another to provide depth contrast as well as visual contrast. Other embodiments may include narrow band emitters such as laser diodes located at predetermined locations within the multi-mode target. These targets may then be used to calibrate various sensors, such as optical sensors, within an inspection system such as a laser ultrasonic inspection system.

12 Claims, 12 Drawing Sheets

SYSTEM AND METHOD TO CALIBRATE MULTIPLE SENSORS

TECHNICAL FIELD OF THE INVENTION

The present invention relates generally to the calibration of inspection sensors, and more particularly, to a system and method for calibrating multiple sensors using a multi-mode target system.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in both the manufacturing processes and after the materials are in service in finished products. Specifically, non-destructive evaluation (NDE) methods must assess the structural integrity of composite materials. This assessment detects inclusions, delaminations and porosities. Conventional NDE methods are slow, labor-intensive, and costly. As a result, testing procedures adversely increase the manufacturing costs associated with composite structures.

Various methods and apparatuses have been proposed to assess the structural integrity of composite structures. One solution uses an ultrasonic source to generate ultrasonic surface displacements in a work piece which are then measured and analyzed. Often, the external source of ultrasound is a pulsed generation laser beam directed at the target. Laser light from a separate detection laser is scattered by ultrasonic surface displacements at the work piece. Collection optics then collect the scattered laser energy. The collection optics are coupled to an interferometer or other device, and data about the structural integrity of the composite structure can be obtained through analysis of the scattered laser energy. Laser ultrasound has been shown to be very effective for the inspection of parts during the manufacturing process. However, the equipment used for laser ultrasound must be precisely calibrated to obtain accurate measurements. Calibration of optical components requires placing calibration targets at specific locations in the inspection field, aiming and focusing the optical systems at the target, and recording optical system data such as lens position, azimuth and elevation. The target is then moved to other locations in the inspection field, and the process is repeated. After repeating the process at multiple locations within the inspection field, algorithms can correlate the camera position in the inspection field.

Additional optics and sensors, such visual cameras, depth cameras, and other like sensors can establish the position and orientation of the work piece. Highly accurate measurements require calibration of the multiple sensors and the ability to correlate measurements to the work piece or final world framework.

Single-mode targets, when used to calibrate equipment, require a different target to calibrate each optical component. This is because each optical component may operate at different wavelengths. A single-mode target, designed to work for one optical sensor, will not function properly as a target for a different optical system operating at a different wavelength. For example, a flat target having a contrasting pattern can serve as a suitable target for an optical camera, but will not serve as a suitable target for a depth camera. The flat target provides no depth contrast. Calibrating each optical sensor independently with a single-mode target is labor intensive, time consuming and can introduce intersection errors in the calibration process. Errors introduced in the calibration process will result in imprecise measurements when the laser ultrasound system is operating in the final world framework.

SUMMARY OF THE INVENTION

The present invention provides a system and method to calibrate a laser ultrasound system using a multi-mode calibration target that substantially addresses the above-identified needs and others.

A multi-mode calibration target may provide both depth and visual contrast in a single target, providing a common focal point for the optical components of a laser ultrasound system. A laser diode may be added to a multi-mode target to provide an additional target mode for optical components of the system. By using a multi-mode calibration target to calibrate the optical sensors of a laser inspection system, a common focal point for many optical systems can be created. By combining several multi-mode targets on a fixed or adjustable array, a multi-mode target array can allow operators to quickly and accurately calibrate multiple sensors prior to using laser ultrasound equipment while limiting the errors associated with calibration.

Prior to performing an ultrasonic inspection, ultrasonic inspection systems must be calibrated. The multi-mode target is operable to calibrate the multiple optical sensors and components without repeating time consuming setups that can introduce differing errors. The multi-mode target may introduce a single multi-mode target, a fixed array of multi-mode targets or an adjustable array of multi-mode targets. The multi-mode target has at least two parallel planar surfaces separated at a distance sufficient to provide depth contrast for depth cameras and contrasting colored surfaces that provide sufficient optical contrast for visual cameras. The parallel planar surfaces may be created by a peg on a first planar surface which elevates a second planar surface above the first planar surface or by inscribing a shape, such as a circle, in a first planar surface to create a second planar surface below the first planar surface. A laser diode may also be included at a specified position to calibrate narrowband detectors such as a visual camera with a notch filter.

The multi-mode target is positioned in the inspection field of the optical components of the system calibrated. After calibration, the multi-mode target may be removed from the inspection field. Materials to be tested using an inspection system, such as a laser ultrasound system, are then placed in the inspection field for inspection.

An inspection system, such as the one described above, may use a laser ultrasound. An external ultrasound source may produce ultrasonic displacements at the surface of the remote target. This external ultrasound source may be a continuous or pulsed laser beam. A detection laser source generates a detection laser beam that is scattered by the ultrasonic displacements. Ultrasonic surface displacements scatter the detection beam to produce phase-modulated light that may be collected and processed to obtain data about the material under test.

The fixed or adjustable array of multi-mode targets enables operators to place an array of multi-mode targets in the inspection field and establish several calibration setpoints for the optical components of the laser ultrasound system. This eliminates the need to move a single target to different parts of the inspection field, saving time and providing greater accuracy in target placement. By reducing or eliminating the need for unique calibration targets for each optical component of the laser ultrasound system that previously each required a unique setup and time consuming calibration procedures, overall system efficiency is improved. Using a multi-mode calibration target provides a common focal point for the optical components and delivers greater accuracy.

Other features and advantages of the present invention will become apparent from the following detailed description of the invention made with reference to the accompanying drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

The present invention provides the ability to use the single multi-mode calibration target to calibrate multiple sensor devices. This multi-mode calibration target may be viewed by sensors such as optical cameras and depth cameras. The multi-mode calibration target may also be used to calibrate ultrasonic sensors. Contrasting colors allow cameras sensitive to visible light to see the target. Additionally, the target may also include depth discontinuities on the surfaces. To calibrate the ultrasonic sensors other discontinuities may be included within the target. For example, discontinuities in density, texture, composition may be used. By having contrasting colors and depth discontinuities on the same target, different visualization or ultrasonic devices may be calibrated or aligned based on the exact same input data. This facilitates the correlation of various data inputs from various sensors. This single multi-mode target is visible to multiple sensor modalities allowing visual elements corresponding to the image of identical world locations to be recognized and correlated while minimizing setup times and errors associated with differing targets. Additionally, a multi-mode target may incorporate other features, such as a laser diode at specified locations on the target. For example, a laser diode may be located at the center of the target where the laser diode is visible only within a narrow band. Such a laser diode may be detected by a camera using a notch filter. Such arrangements have been used in structured light range cameras.

Figure 1:
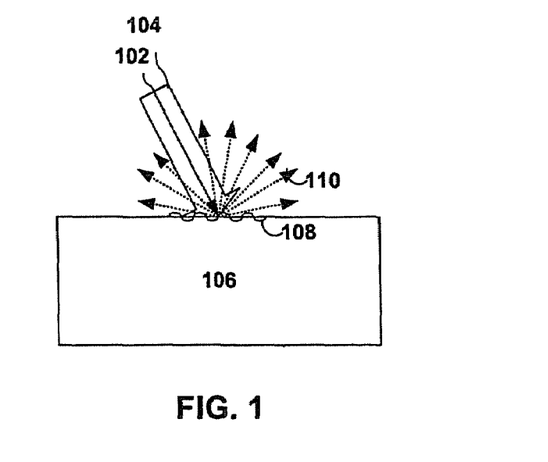
FIG. 1 illustrates the use of generation laser beam and a detection laser beam to generate and detect laser ultrasonic displacements in accordance with an embodiment of the present invention.

FIG. 1 depicts two incoming laser beams that generate and detect laser ultrasonic displacements. Laser beam 102 generates ultrasound while illumination laser beam 104 detects the ultrasound at a remote target 106, such as a composite material under test. As shown, these lasers may be coaxially applied to remote target 106. Generation laser beam 102 causes thermo-elastic expansion in target 106 that results in the formation of ultrasonic deformations 108. Deformations 108 modulate, scatter and reflect illumination laser beam 104 to produce phase-modulated light 110 directed away from target 106 which is collected and processed to obtain information of the internal structure of remote target 106.

Figure 2:
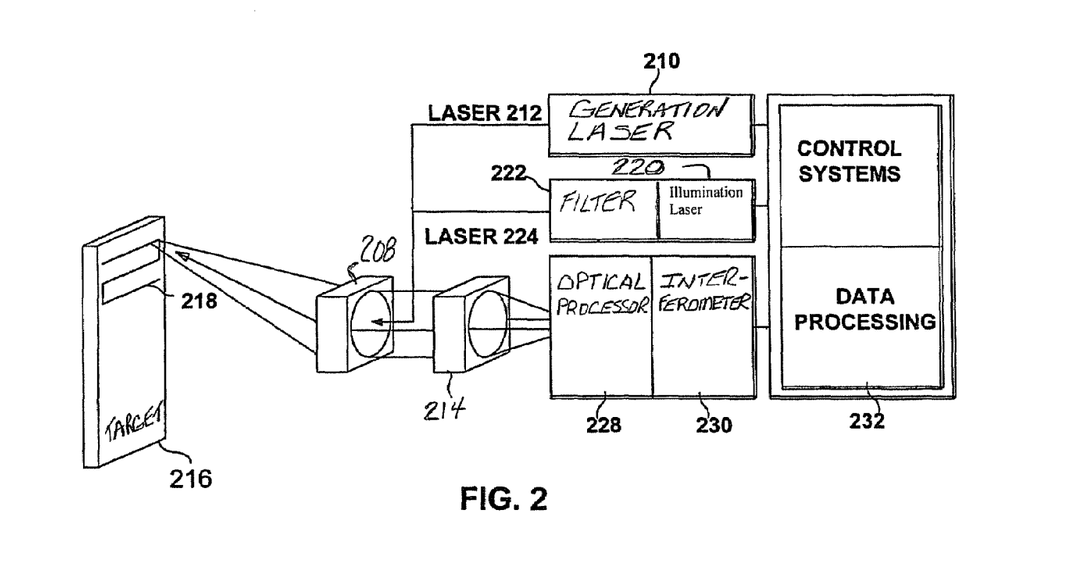
FIG. 2 provides a block diagram to show the basic components of laser ultrasound system.

FIG. 2 provides a block diagram with the basic components for performing ultrasonic laser testing. Generation laser 210 produces laser beam 212 which optical assembly 214 directs to target 216. As shown, optical assembly 214 includes a scanner or other like mechanism that moves laser beam 212 along a scan or test plan 218. Optical assembly 214 may include visual cameras, depth cameras, range detectors, narrowband cameras or other like optical sensors known to those having skill in the art. These optical sensors each may require calibrations prior to performing an inspection. This calibration verifies the ability of the system to integrate information gathered by various sensors. Generation laser 210 produces an ultrasonic wave 108 within target 216.

The ultrasonic wave is the result of thermo-elastic expansion of the composite material as the material absorbs the generation laser beam. Composite material 216 readily absorbs generation laser beam 212 without ablating or breaking down. Higher powered generation lasers are not necessarily preferred to overcome SNR issues as these can result in ablation. In other embodiments, depending on the material being tested, some ablation may be acceptable in order to increase the SNR of the detected signal. Generation laser beam 212 has appropriate pulse duration to induce ultrasonic surface deformations. For example, a transverse-excited atmospheric (TEA) $CO_2$ laser can produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. Generation laser beam 212 absorbs as heat into the target surface thereby causing thermo-elastic expansion without ablation.

Illumination laser 220 operates in pulsed mode or continuous wave mode as to not induce ultrasonic displacements. For example, an Nd:YAG laser can be used. The power of this laser must be sufficient to deliver, for example, a 100 milli-joule, 100 micro-second pulse, which may require a one kilo-watt laser. Illumination laser 220 generates detection laser beam 224. Illumination laser 220 includes or optically couples to filtering mechanism 222 to remove noise from detection laser beam 224. Optical assembly 214 directs illumination laser beam 220 to the surface of composite material 216 which scatters and/or reflects detection laser beam 224.

Resultant phase modulated light is collected by collection optics disposed in collection optics 214. As shown here, scattered and/or reflected illumination laser travels back through optical assembly 214. Optional optical processor 228 and interferometer 230 process the phase modulated light to produce a signal containing information representative of the ultrasonic displacements at the surface of composite material 216. Data processing and control system 232 coordinate operation of the laser ultrasound system components.

Data processing and control system 232 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated in FIG. 8.

Figure 3A:
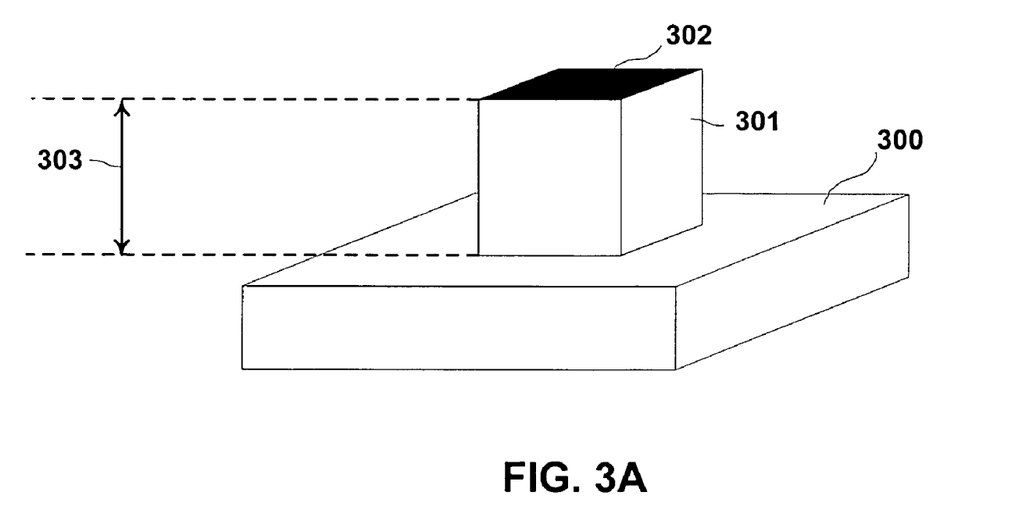
FIGS. 3A, 3B and 3C depict a multi-mode target having raised planar surfaces formed with square or rectangular pegs.
Figure 3B:
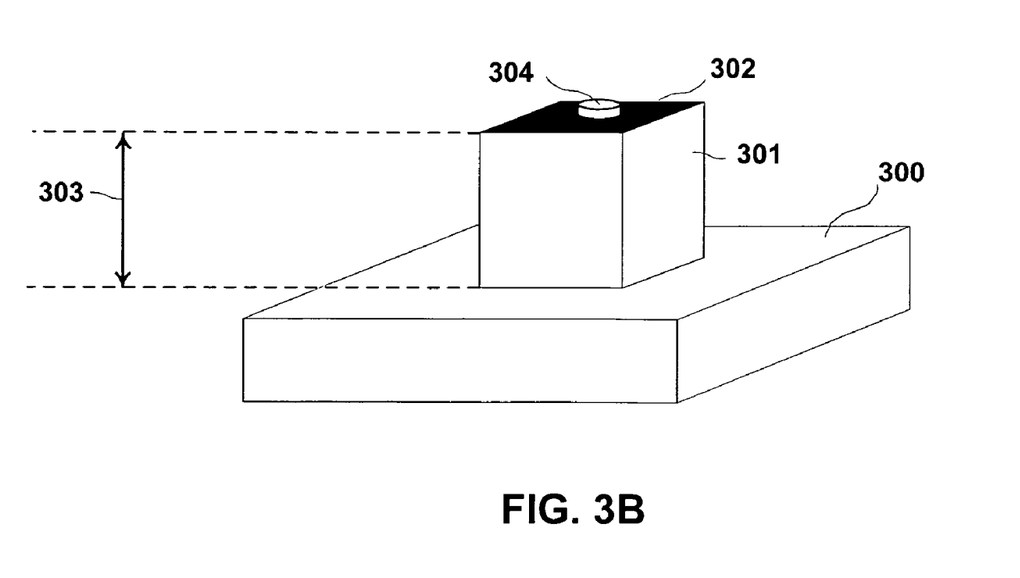
Figure 3C:
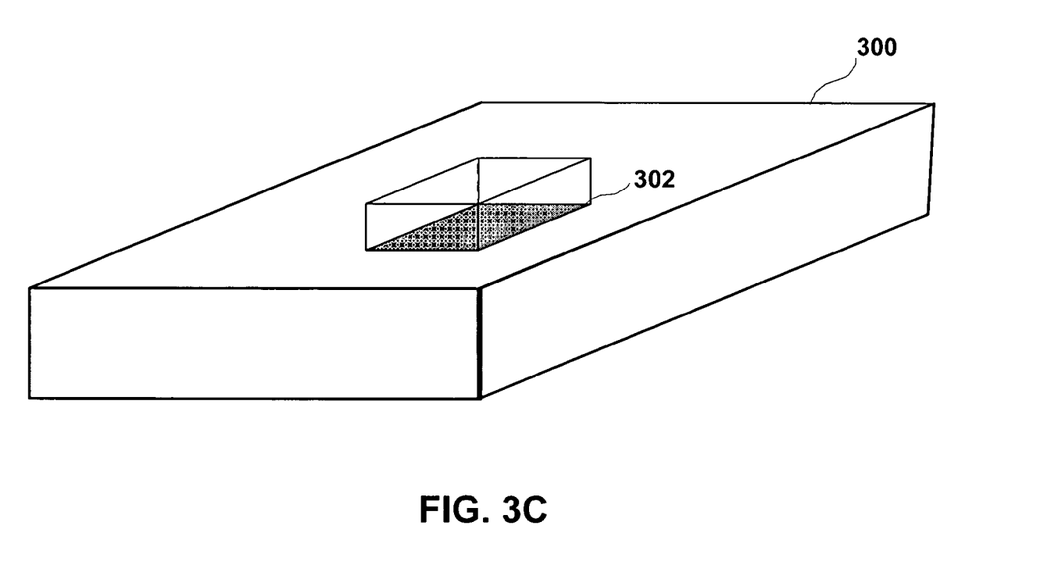

FIGS. 3A, 3B, and 3C depict embodiments of multi-mode targets having or with raised or recessed planar surface that provide depth discontinuities in the target surface. These discontinuities are provided here by square or rectangular pegs or recesses. Target 300 may be constructed from a material having a construction similar to that of the objects to be inspected. Target 300 may be made from a material suitable for laser ultrasound inspection, such as carbon fiber composite material. This material may be milled to form planar surface 300, square or rectangular peg 301 and planar surface 302. Planar surfaces 300 and 302 are parallel to one another and separated by square or rectangular peg 301 at distance 303. Distance 303 is an appropriate distance to provide suitable depth contrast to calibrate depth cameras. Planar surface 302 is painted a contrasting color to provide sufficient visual contrast between planar surface 302 and planar surface 300 to calibrate visual cameras. FIG. 3B depicts the multi-mode laser target of FIG. 3A and adds laser diode 304 at the target center. Laser diode 304 is visible from narrow band detectors such as a camera with a notch filter.

Figure 4A:
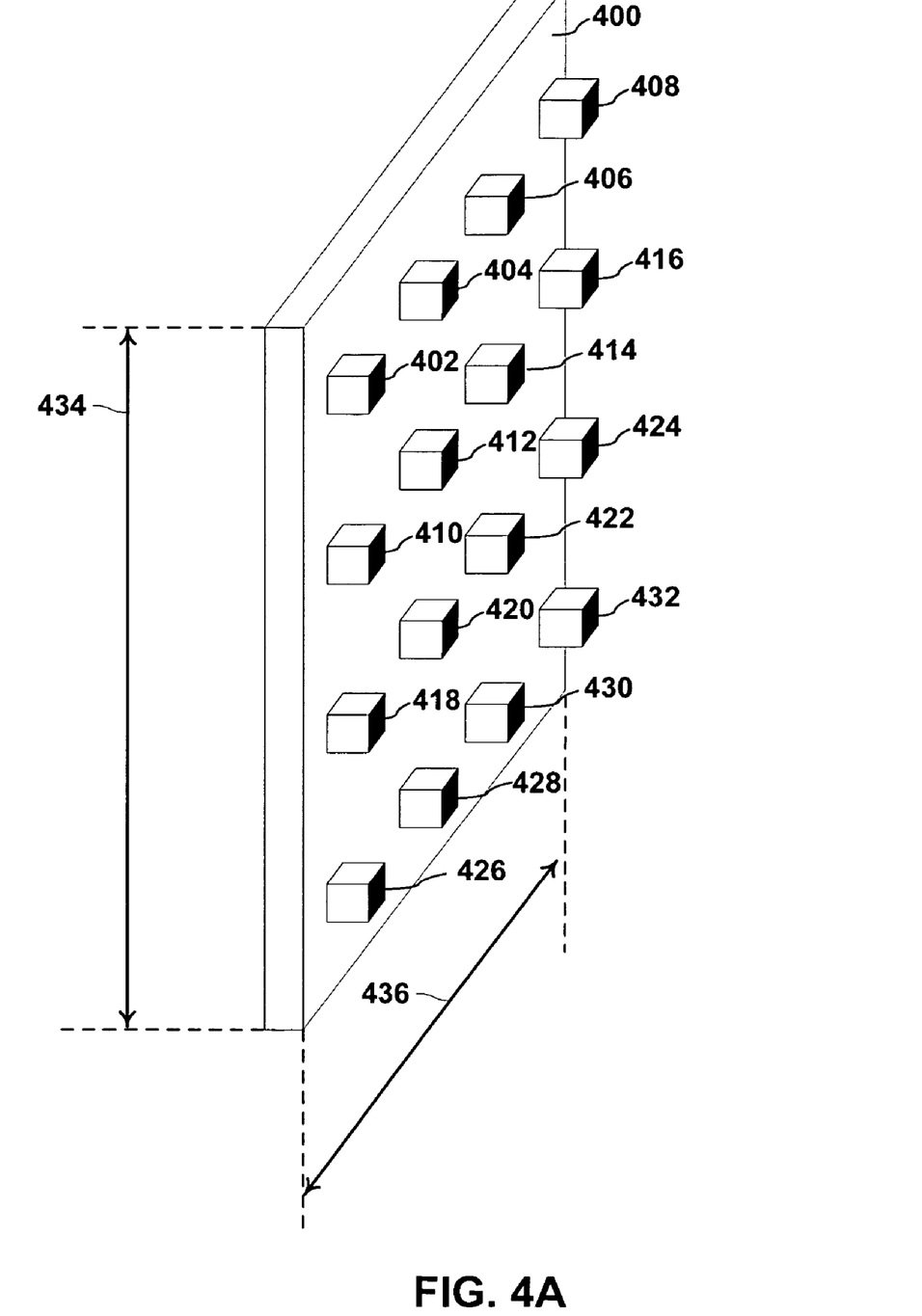
FIG. 4A depicts a symmetrical fixed array of multi-mode targets having multiple square or rectangular pegs to provide raised planar surfaces.

FIG. 4A illustrates a fixed array of multi-mode targets built with square or rectangular pegs. Material suitable for laser ultrasound inspection, such as carbon fiber composite material, is milled to form planar surface 400 and square or rectangular pegs 402, 404, 406, 408, 410, 412, 414, 416, 418, 420, 422, 424, 426, 428, 430, and 432. The square or rectangular pegs are milled to height 434 and width 436 and painted to form multi-mode targets. as described in FIGS. 3A and 3C. The painted surfaces provide optical contrast when compared to planar surface 400. These pegs provide raised planar surfaces having depth discontinuities when compared to planar surface 400. Some or all of the multi-mode targets may include a laser diode to add an additional modality to the multi-mode targets as described in FIG. 3B. The fixed array of multi-mode targets contrasting heights and colors are suitable to calibrate the optical sensors of an inspection system such as the laser ultrasound system of FIG. 2.

Figure 4B:
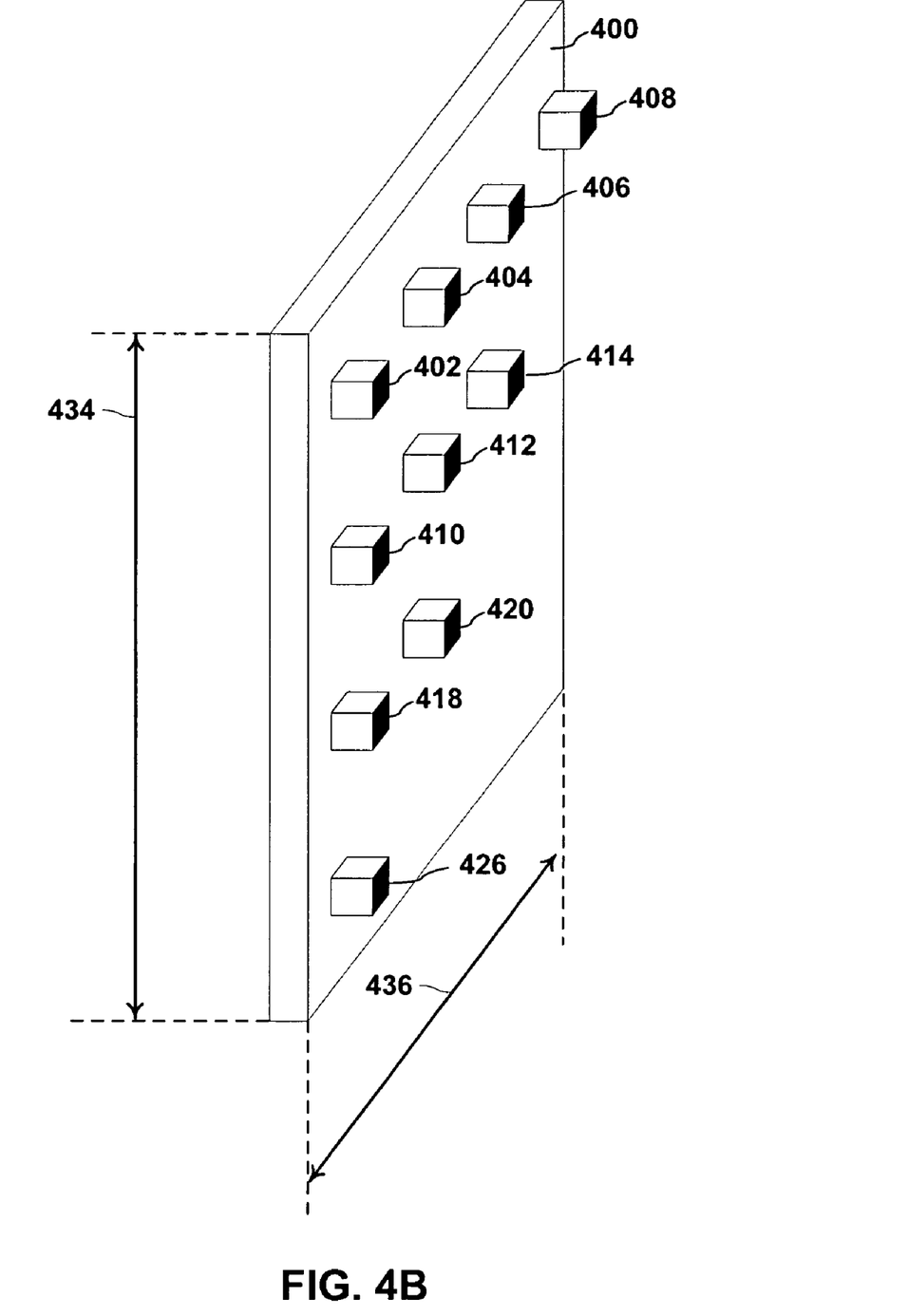
FIG. 4B depicts an asymmetrical fixed array of multi-mode targets having multiple square or rectangular pegs to provide raised planar surfaces.

FIG. 4B illustrates another fixed array of multi-mode targets built with square or rectangular pegs. This array is asymmetrical when compared to the array of FIG. 4A. Planar surface 400 and square or rectangular pegs 402, 404, 406, 408, 410, 412, 414, 418, 420, and 426. The square or rectangular pegs are milled to height 434 and width 436 and painted to form multi-mode targets as described in FIGS. 3A and 3C. The positioning of these pegs on planar surface 400 has a unique orientation. When the asymmetric pattern is recognized, the orientation of the optical sensors relative to the target also becomes known. Some or all of the multi-mode targets may include a laser diode that may also be asymmetrically located on the planar surface to add an additional modality to the multi-mode targets.

Figure 5:
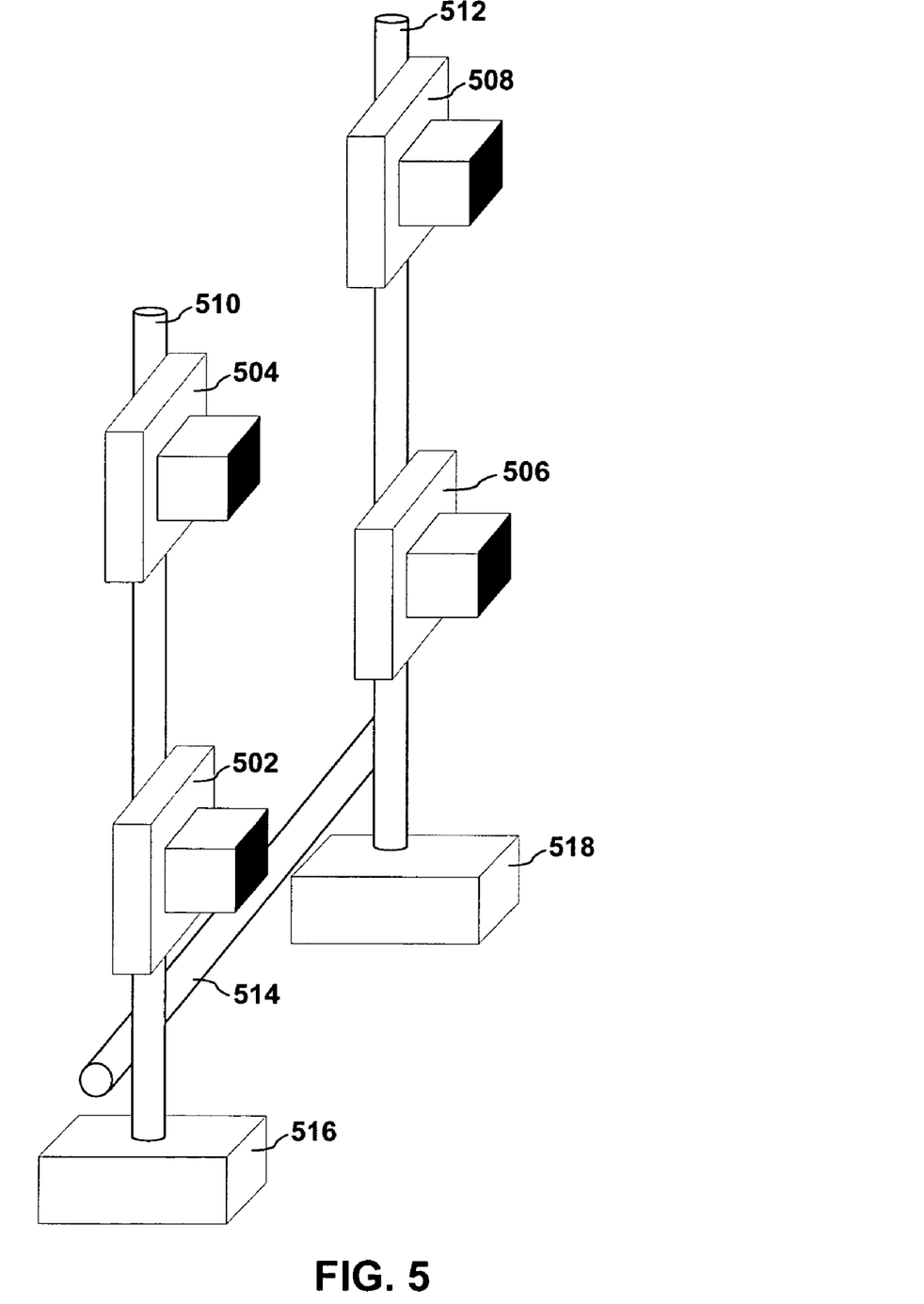
FIG. 5 provides an adjustable array of multi-mode targets having raised planar surfaces formed from square or rectangular pegs.

FIG. 5 illustrates an adjustable array of multi-mode targets built with square or rectangular pegs as depicted in FIGS. 3A and 3B. Multi-mode targets 502, 504, 506 and 508 are adjustably mounted on posts 510 and 512. This type of mounting allows multi-mode targets 502, 504, 506 and 508 to be moved and adjusted to change the size of the target array. As shown, the array includes contrasting colors and depth discontinuities. However, other embodiments may support other modalities as known to those having skill in the art. For example, the multi-mode targets may include a laser diode at a predetermined location to form a multi-mode target as described in FIG. 3B. Posts 510 and 512 may allow multi-mode targets 502, 504, 506 and 508 to be repositioned vertically. Bar 514 may allow the horizontal separation between posts 510 and 512 to be adjusted as well to change the size of the target array. Posts 510 and 512 mechanically couple to support stands 516 and 518.

Figure 6A:
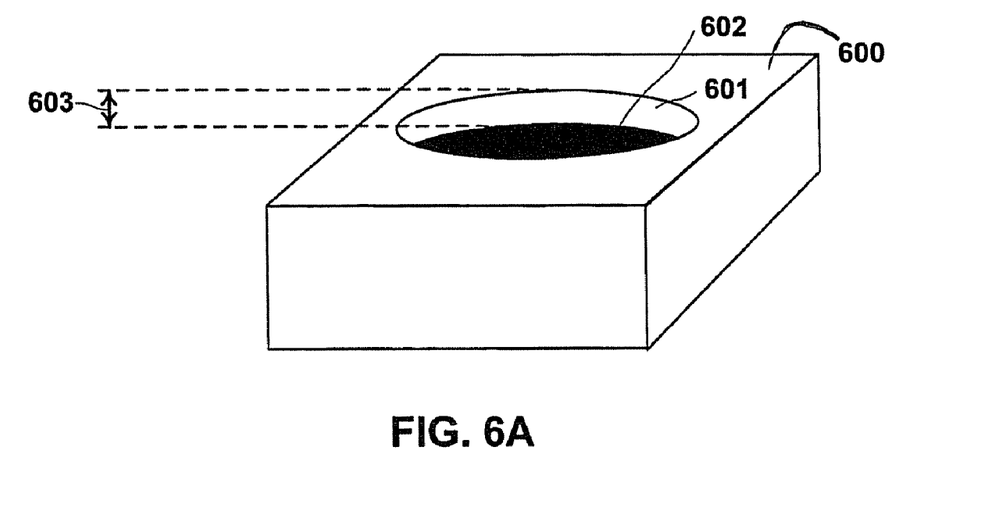
FIGS. 6A and 6B depict of a multi-mode target built with an inscribed or recessed circular planar surface.
Figure 6B:
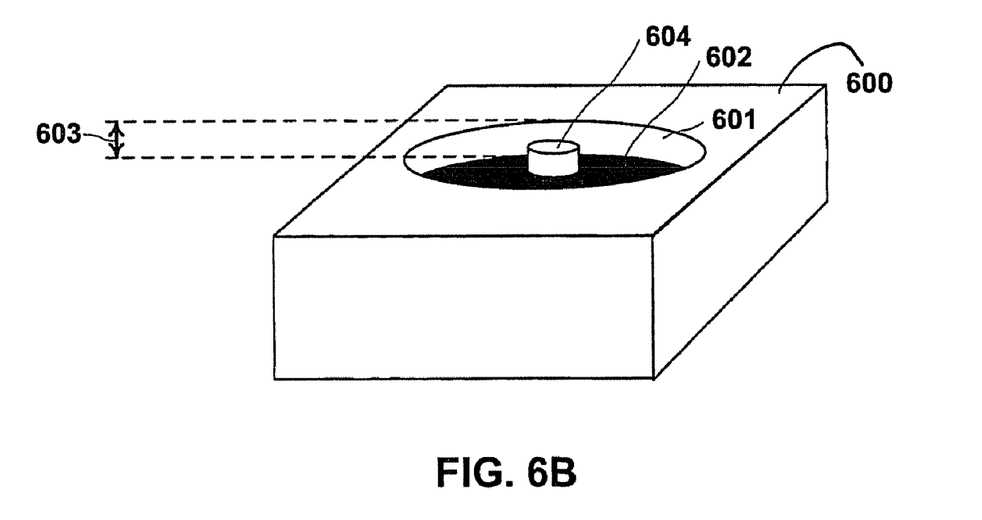

FIGS. 6A and 6B depict an embodiment of a multi-mode target having an inscribed circle. The inscribed or raised surface may be an irregular or regular polygon, circle, ellipse or other like shape known. Material suitable for laser ultrasound inspection, such as carbon fiber composite material, is milled to form planar surface 600, inscribed circle 601 and planar surface 602. Planar surfaces 600 and 602 are parallel to one another and separated at distance 603. Distance 603 is an appropriate distance to provide suitable depth contrast to calibrate depth cameras. Planar surface 602 and planar surface 600 have contrasting colors to provide sufficient visual contrast between planar surface 602 and planar surface 600 to calibrate visual cameras or other like optical sensors. FIG. 6B adds laser diode 604 at the target center. Laser diode 604 is visible from narrow band detectors such as a camera with a notch filter.

Figure 7:
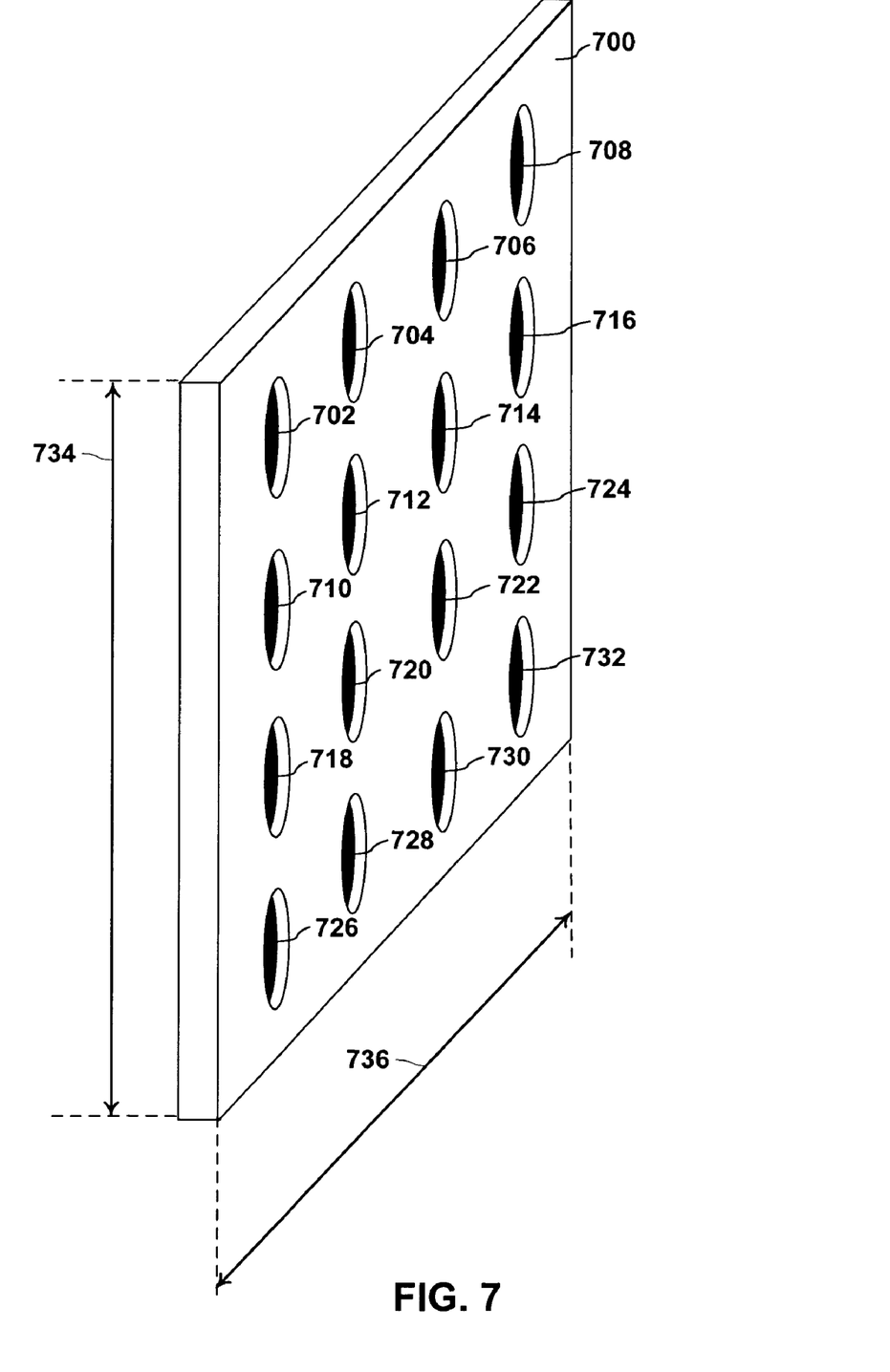
FIG. 7 depicts a fixed array of multi-mode targets having recessed planar surfaces.
Figure 8:
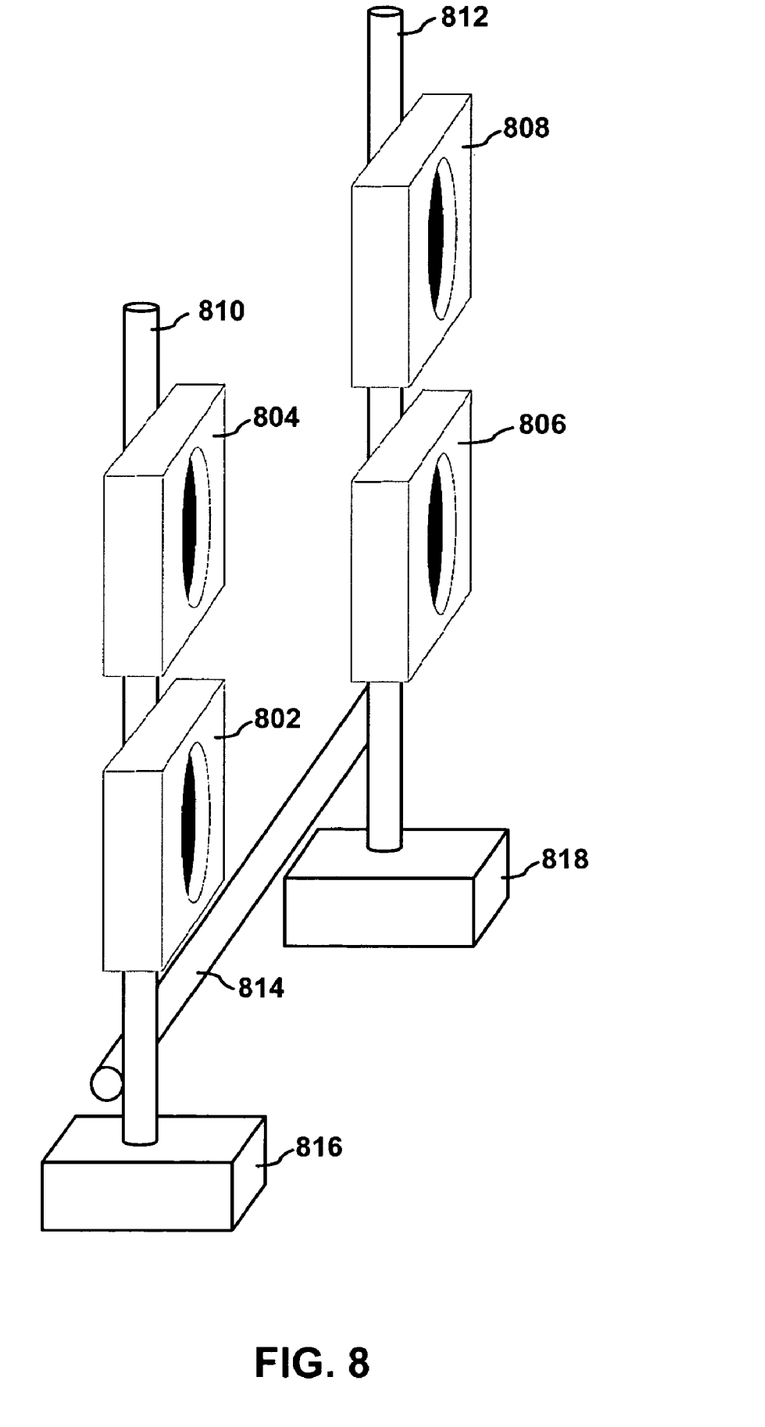
FIG. 8 illustrates an adjustable array of multi-mode targets having recessed planar surfaces.

FIG. 7 depicts a fixed array of multi-mode targets such as the inscribed circles of FIG. 6A. Although the described embodiments depict the raised or recessed planar surfaces as squares, rectangles or circles, any shape may be chosen. As previously described, target 700 may be fabricated from a material like the materials to be tested. In these embodiments carbon fiber composite material is milled to form planar surface 700 and recesses 702, 704, 706, 708, 710, 712, 714, 716, 718, 720, 722, 724, 726, 728, 730, and 732 are inscribed in the surface. These recesses have a floor parallel to planar surface 700. Additionally, the floor of the recesses may be painted to form multi-mode targets as described in FIG. 6A. Some or all of the multi-mode targets may include laser diode(s) to add additional modalities to the array. FIG. 8 illustrates an adjustable array of multi-mode targets built with circular recesses as depicted in FIGS. 6A and 6B. Multi-mode targets 802, 804, 806 and 808 are adjustably mounted on posts 810 and 812. This type of mounting allows multi-mode targets 802, 804, 806 and 808 to be moved and adjusted to change the size of the target array. As shown, the array includes contrasting colors and depth discontinuities. However, other embodiments may support other modalities as known to those having skill in the art. For example, the multi-mode targets may include a laser diode at a predetermined location to add an additional modality to the multi-mode target. Posts 810 and 812 may allow multi-mode targets 802, 804, 806 and 808 to be repositioned vertically. Bar 814 may allow the horizontal separation between posts 810 and 812 to be adjusted as well to change the size of the target array. Posts 810 and 812 mechanically couple to support stands 816 and 818.

Figure 9:
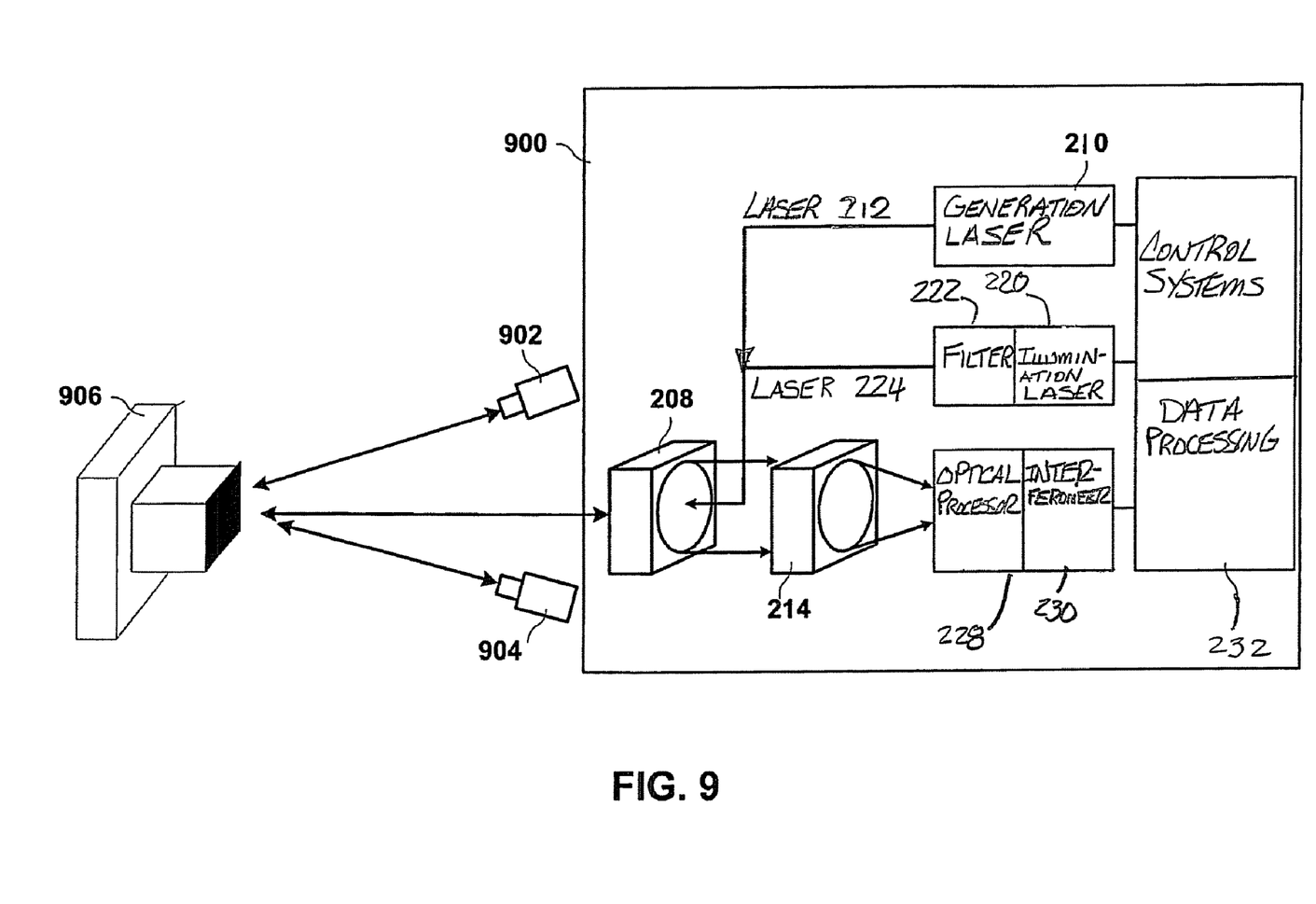
FIG. 9 illustrates the use of multi-mode targets and multi-mode target arrays in calibrating a laser ultrasound system.

FIG. 9 illustrates a laser ultrasonic inspection system that uses multi-mode targets and/or multi-mode target arrays in calibrating the laser ultrasonic inspection system. Laser ultrasonic inspection system 900, as depicted in FIG. 2, is combined with optical camera 902 and range camera 904. Optical assembly 208 of laser ultrasonic inspection 900, optical camera 902 and range camera 904 are focused on multi-mode target 906. Information from laser ultrasonic inspection 900, optical camera 902, range camera 904, narrowband cameras, and/or other like optical sensors are combined in control module 220 to calibrate the system. The system is calibrated by comparing and correcting the measured results to the known information associated with the multimode target. This allows information gathered from various sensors associated with a single location during actual testing to be properly correlated while minimizing location errors. During calibration, any combination of individual or arrays of multi-mode targets, as described above, may be used.

Figure 10:
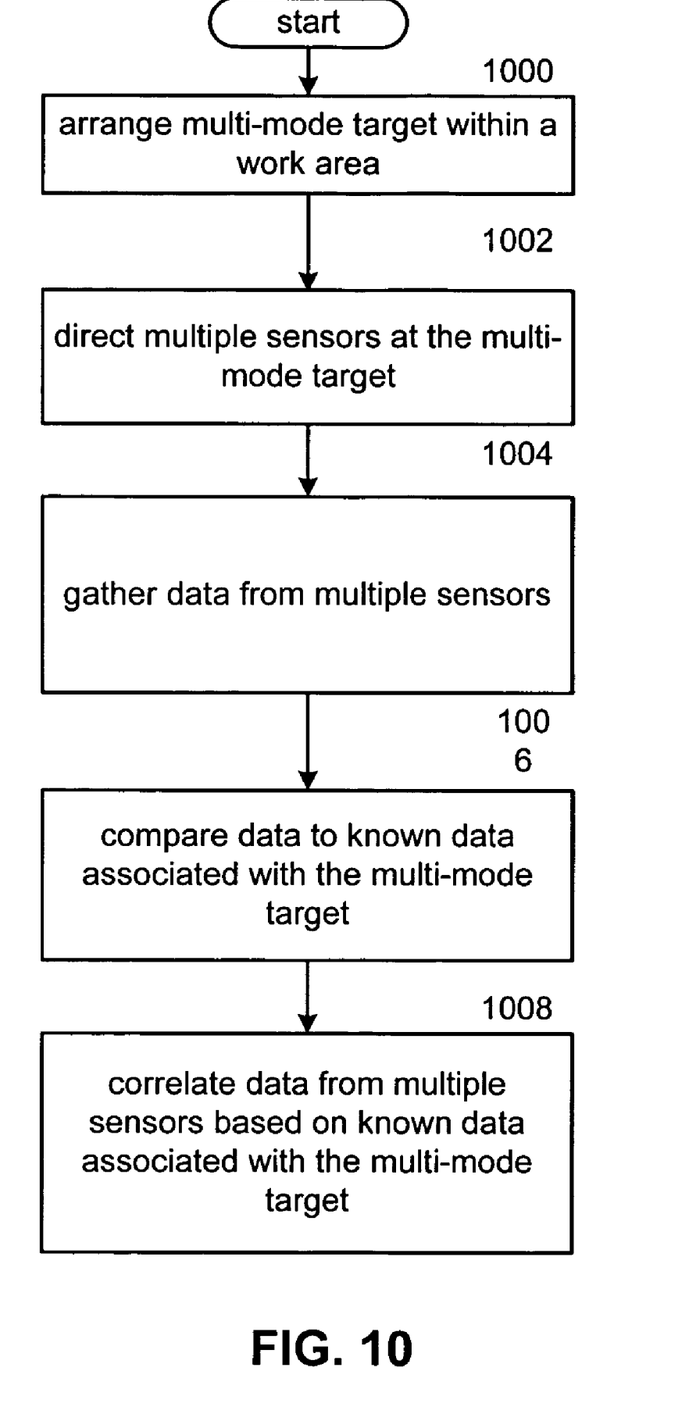
FIG. 10 provides a logic flow diagram illustrating a calibration procedure in accordance with an embodiment of the present invention.

FIG. 10 provides a logic flow diagram illustrating a method of calibrating multiple optical sensors using a multi-mode target. This involves first arranging multi-mode targets at predetermined locations within a work area in step 1000. Step 1002 directs multiple optical sensors, or other sensors known to those having skill in the art, at the multi-mode target. Step 1004 gathers data from the multiple sensors. The data is compared to known data associated with the multi-mode target in step 1006. The optical data from the multiple optical sensors is correlated based on the known data.

Figure 11:
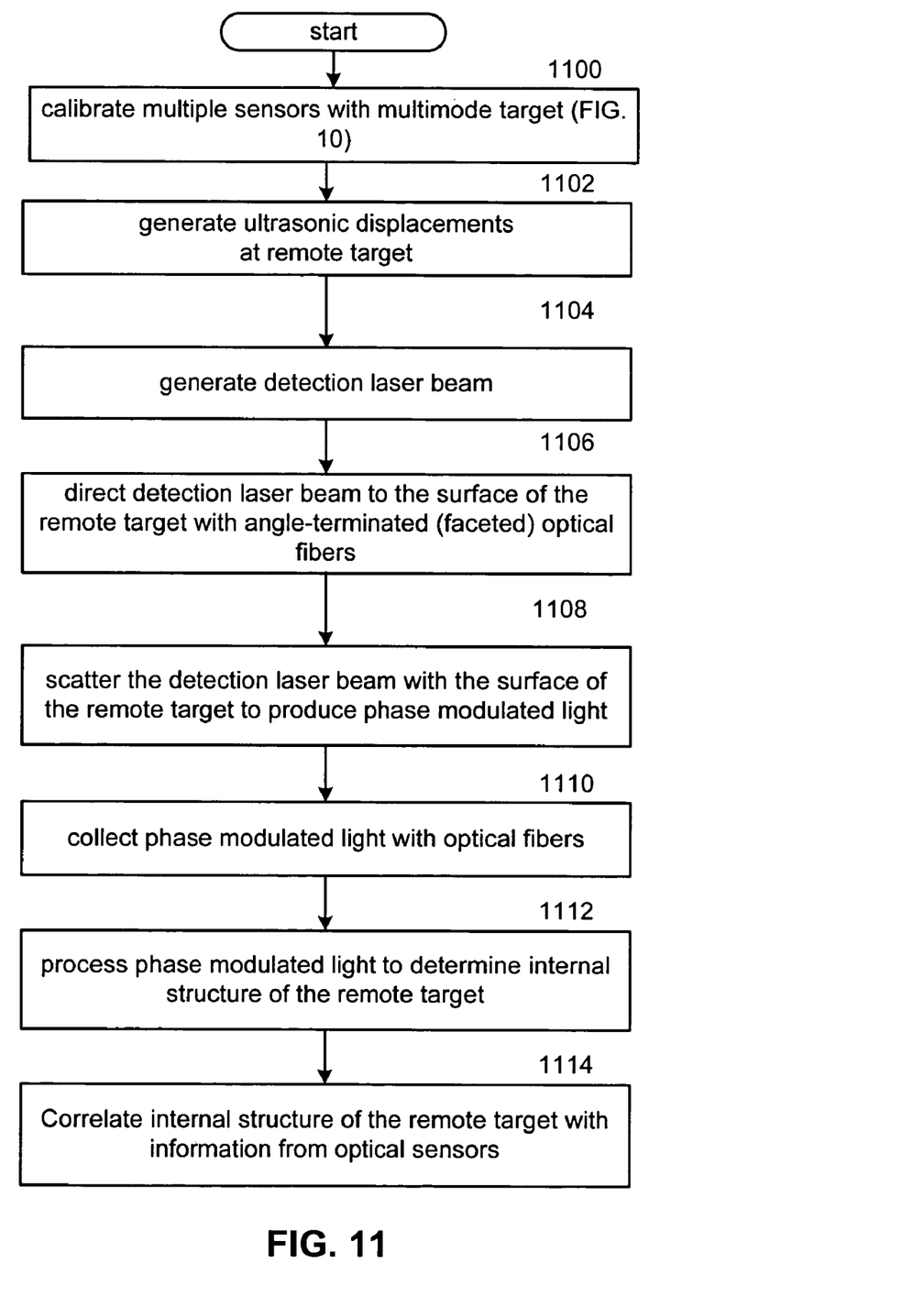
FIG. 11 provides a logic flow diagram illustrating a method to perform laser ultrasonic inspections using a system calibrated in accordance with an embodiment of the present invention.

FIG. 11 provides a logic flow diagram illustrating a method to perform laser ultrasonic inspections of a remote target. This involves first calibrating multiple sensors, such as, but not limited to the multiple optical sensors associated with a laser ultrasonic inspection system such as the depth and visualization cameras of FIG. 9. This calibration may be performed in accordance with the method presented in FIG. 10 or a similar method known to those having skill in the art.

Ultrasonic surface displacements are generated at a surface of the remote target in step 1102. In step 1104, a detection laser beam is generated for delivery to the surface of a remote target in step 1106. In step 1108, the remote target then scatters the detection laser beam with ultrasonic surface displacements at its surface to produce phase-modulated light. The phase-modulated light is collected at step 1110. Then the phase modulated light is processed in step 1112 to obtain data representative of the ultrasonic surface displacements at the surface. This data may be correlated with that of other optical sensors for further analysis and visualization in step 1114.

In operation the present invention allows laser ultrasonic test equipment to be used in a wider range of environments while testing more complex surfaces or surfaces within limited access areas. The present invention also allows existing laser ultrasound equipment to be modified to test more complex surfaces or surfaces within limited access areas without replacing the existing detection laser, an expensive component in the laser ultrasound system.

The multi-mode target may be fabricated from the material for which the inspection system the optical sensors will be examining. Such as in the example of the laser ultrasonic system, the multi-mode target may be fabricated of carbon fiber composite material. This multi-mode target places the various calibration targets associated with individual optical sensors within a single world framework in order to ensure that the multiple sensors work well together. This also helps eliminate positioning or setup errors associated with performing individual calibrations. It should be noted that the embodiments discussed here and above have specifically shown that the multi-mode targets are used with different optical modalities. However, it should be understood that the multi-mode target may incorporate calibration targets for other types of sensors such as sonic, tactile, radio frequency, or other like sensor platforms known to those having skill in the art. Thus, this multi-mode target allows different sensor devices to be calibrated or aligned based on input data gathered from identical locations on the target. Processing algorithms executed by processors can determine and calibrate the multiple sensors based on the multiple views of the target provided by the multiple sensors. These processors are able to correlate signals from the multiple sensor modalities allowing individual elements (for example, pixels) corresponding to the image of identical locations in the frame of the work area to be recognized and used for subsequent analysis.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method to generate and detect ultrasonic surface displacements at a remote target comprising:
   a. providing a laser ultrasonic inspection system having a generation laser, a detection laser, and an optical sensor;
   b. providing a multi-mode calibration target having known optical contrast, depth discontinuities, and different shapes;
   c. calibrating the optical sensor in the laser ultra-sonic inspection system by viewing the calibration target with the optical sensor and comparing and correcting results of the viewing with known information about the multi-mode target;
   d. generating ultrasonic displacements at a surface of the remote target;

e. generating a detection laser beam; directing the detection laser beam to the surface of the remote target;

f. scattering the detection laser beam with the ultrasonic surface displacements at the remote target surface to produce phase modulated light;

g. collecting the phase modulated light;

h. processing the phase modulated light to obtain data representative of the ultrasonic surface displacements at the surface;

i. establishing the position of the target using the calibrated optical sensor; and j. correlating the data of step (h) with the position of step (i) so that the surface displacements detected correspond to their location on the target.

2. The method of claim 1, wherein the depth discontinuities comprise raised portions having distinctive shapes, wherein the shapes comprise a form selected from the list consisting of a square, a rectangle, patterns of shapes, regular polygons, irregular polygons, circles, and ellipses.

3. The method of claim 2, wherein the at least one calibration target is an array of targets.

4. The method of claim 1, wherein the optical sensor comprises a sensor selected from the list consisting of a depth camera, a visual camera, an optical camera, a narrow band camera, and combinations thereof.

5. The method of claim 1, further comprising providing a processor with an algorithm and performing the correlating of step (j) using the processor.

6. A laser ultrasonic inspection system operable to detect ultrasonic displacements at a remote target, comprising:

an optical sensor;

a detection laser having a detection laser beam;

a multi-mode calibration target comprising surface depth discontinuities and visual contrast configured to provide calibration for the optical sensor, wherein the optical sensor views and measures the calibration target;

a first optical assembly that receives and directs the detection laser beam to the remote target where ultrasonic displacements at the remote target scatter the detection laser beam to produce phase modulated light having measured information representative of the remote target structure;

an interferometer to process the phase modulated light from the remote target and generate at least one output signal for each phase modulated light; and a processor operable to process the at least one output signal to obtain data representative of the ultrasonic displacements at the remote target; process information contained within the phase modulated light from the remote target; calibrate the system by comparing and correcting the measured information from the optical sensor representative of the multi mode calibration target structure to the known multi mode calibration target structure, and correlate location of the ultrasonic displacement on the remote target based on calibrating.

7. The laser ultrasonic inspection system of claim 6, wherein the multi-mode calibration target comprises: a first planar surface, having a first color; and a second planar surface having a second color that contrasts with the first color, wherein: the second planar surface is parallel to the first planar surface; and the second planar surface is raised or recessed from the first planar surface.

8. The laser ultrasonic inspection system of claim 6, further comprising a laser diode located at a predetermined location in the multi-mode calibration target.

9. The laser ultrasonic inspection system of claim 7, wherein the first planar surface is fabricated of the material comprising the target.

10. The laser ultrasonic inspection system of claim 9, wherein the material comprises composite materials.

11. The laser ultrasonic inspection system of claim 6, further comprising a discontinuity for calibrating an ultrasonic sensor selected from the list consisting of a discontinuity in density, discontinuity in texture, and discontinuity in composition.

12. The laser ultrasonic inspection system of claim 6 wherein the optical sensor comprise a device selected from the list consisting of a depth camera, a visual camera, a narrow band camera, and combinations thereof.

* * * * *